United States Patent [19]

Garwood et al.

[11] Patent Number: 4,788,375

[45] Date of Patent: Nov. 29, 1988

[54] OLEFIN CONVERSION TO LUBRICANT RANGE HYDROCARBONS

[75] Inventors: William E. Garwood, Haddonfield; Guenter G. Kuehl, Cherry Hill; Rene B. LaPierre, Medford, all of N.J.

[73] Assignee: Mobil Oil Corporation, New York, N.Y.

[21] Appl. No.: 125,906

[22] Filed: Nov. 27, 1987

[51] Int. Cl.$^4$ .............................................. C07C 2/02
[52] U.S. Cl. ................................................... 585/533
[58] Field of Search ........................................ 585/533

[56] References Cited

U.S. PATENT DOCUMENTS

| | | | |
|---|---|---|---|
| 4,454,367 | 6/1984 | Sakurada et al. | 585/533 |
| 4,465,884 | 8/1984 | Degnan et al. | 585/415 |
| 4,517,399 | 5/1985 | Chester et al. | 585/533 |
| 4,520,221 | 5/1985 | Chen | 585/517 |
| 4,547,613 | 10/1985 | Garwood et al. | 585/533 |

FOREIGN PATENT DOCUMENTS 98040 11/1984 European Pat. Off. .

OTHER PUBLICATIONS

ACS, Advances in Chemistry, No. 121 (1973), G. T. Kerr.

*Primary Examiner*—Curtis R. Davis
*Attorney, Agent, or Firm*—Alexander J. McKillop; Michael G. Gilman; L. G. Wise

[57] ABSTRACT

An improved process for the production of a high viscosity index lubricant range oil in high yield by contacting light olefins under oligomerizing conditions with a zeolite type catalyst, such as ZSM-5, which has been extracted with a metal chelating agent to remove a portion of framework metal oxide.

16 Claims, No Drawings

OLEFIN CONVERSION TO LUBRICANT RANGE HYDROCARBONS

FIELD OF THE INVENTION

This invention relates to a process for the production in improved yield of a high viscosity index lubricating oil fraction using a fixed bed catalyst reactor with zeolite type catalyst. More particularly, this invention relates to a process for the manufacture of an improved yield of a high viscosity index lubricating oil by the oligomerization of lower olefins over ZSM-5 zeolite catalyst treated with a metal chelating agent.

BACKGROUND OF THE INVENTION

The conversion of olefins over ZSM-5 type catalyst is known in the art and is the subject of many patents. A wide range of techniques have been disclosed leading to the improved production of gasoline, distillates and lubricant range hydrocarbons through catalyst modifications, unique process conditions and the like. For example, U.S. Pat. No. 4,227,992 and the patents therein are excellent examples of the prior art in connection with this general subject.

In U.S. Pat. No. 4,517,399 to Chester et al, olefins are oligomerized over ZSM-5 type zeolite catalyst to obtain high viscosity index lubricating oils wherein the improvement involves the use of large crystal size ZSM-5.

In U.S. Pat. No. 4,547,613 to Garwood et al., light olefins are converted into a high viscosity index lubricating oil by contacting at elevated pressure with ZSM-5 type catalyst that has been conditioned by treatment with a light hydrocarbon gas at low pressure and elevated temperature.

In U.S. Pat. No. 4,520,221 to Chen, a process is disclosed providing high yields of lubricating oils with substantially higher viscosity indices from the conversion of light olefins such as propylene using ZSM-5 catalyst. The results are achieved by removing the surface acidity of the catalyst by treatment with a bulky amine. U.S. Pat. No. 4,568,786 to Chen et al. discloses a continuous process for the conversion of olefins to heavier hydrocarbons containing a lubricant fraction of high viscosity index by cofeeding a surface deactivating agent such as a bulky amine.

Some work has been reported on the dealuminization of zeolites using chelating agents resulting in an apparent increase in acidic activity of Bronsted Acid type. EDTA has been reported as a useful chelating agent for increasing the silia to aluminia ratio in zeolite. This work is reported in part by G. T. Kerr in A.C.S. publication Advances In Chemistry Series, Number 121 (1973), which publication is incorporated herein by reference. Such partly dealuminized zeolite catalysts have been considered to possess improved activity as cracking catalysts.

In the instant invention it has been surprisingly discovered that high yields of high viscosity index lubricant range oils can be produced by polymerizing or oligomerizing light olefins in contact with a metallosilicate catalyst, such as ZSM-5, that has been extracted with a metal chelating agent.

SUMMARY OF THE INVENTION

In the present invention it has been discovered that in the process of converting light olefins, such as $C_3$ to $C_9$ olefins, to lubricant range hydrocarbons comprising contacting the light olefins at high pressures and elevated temperature, high yields can be achieved when the light olefin feedstream is contacted with a medium pore size shape selective metallosilicate solid zeolite catalyst that has been extracted with a metal chelating agent. The improvement produces a $C_{20}+$, hydrocarbon fraction comprising a major portion of 650° F.+ lubricant range hydrocarbons with a high viscosity index.

Generally the improved process for the conversion of light olefins to $C_{20}+$ lubricant range hydrocarbons in high yield comprises, providing a medium pore size shape selective aluminosilicate zeolite type catalyst having Bronsted Acid activity and the structure of ZSM-5. This catalyst is treated, usually by extraction, with an aluminum chelating agent under conditions sufficient to reduce the framework $Al_2O_3$ content of the catalyst by about 25% of the total $Al_2O_3$ Contacting the light olefins with the extracted catalyst under oligomerizing conditions of high pressure and elevated temperature produces an effluent stream comprising a major portion of $C_{20}+$ hydrocarbon. The $C_{20}+$ hydrocarbons are separated to provide a high yield of 343°+ C. (650° F.) hydrocarbons that exhibit a high viscosity index.

A wide variety of chelating agent are effective in the present invention to reduce catalyst framework $Al_2O_3$. These include bidentate, tridentate and polydentate metal chelating agents, most notably EDTA.

DESCRIPTION OF SPECIFIC EMBODIMENTS

The shape-selective oligomerization/polymerization catalysts preferred for use herein following extraction include the crystalline aluminosilicate zeolites having a silica to alumina molar ratio of at least 20 and a constraint index of about 1 to 12. Representative of the ZSM-5 type zeolites are ZSM-5, ZSM-11, ZSM-12, ZSM-23, ZSM-35, and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. Nos. 3,832,449 for ZSM-12; 4,076,842 for ZSM-23; 4,016,245 for ZSM-35 and 4,046,839 for ZSM-38. The disclosures of these patents are incorporated herein by reference. A suitable shape selective medium pore catalyst for fixed bed is a small crystal H-ZSM-5 zeolite (silica:alumina ratio=70:1) with alumina binder in the form of cylindrical extrudates of about 1–5 mm. Unless otherwise stated in this description, the pre-extraction catalyst shall consist essentially of ZSM-5, which has a crystallite size of about 0.02 to 0.05 micron.

Shape-selective oligomerization, as it applies to the conversion of $C_2$-$C_9$ olefins over ZSM-5, is known to produce higher olefins up to $C_{20}$ and higher. As reported by Garwood in Intrazeolite Chemistry 23, (Amer. Chem. Soc., 1983), reaction conditions favoring higher molecular weight product are low temperature, elevaed pressure, and long contact time. The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of ZSM-5 type catalysts impose shape-selective constraints on the configuration of the large molecules, accounting for the differences with other catalysts.

An important characteristic of the crystal structure of the zeolites for use herein is that they provide constrained access to, and egress from, the intracrystalline free space by virtue of having a pore dimension greater than about 5 angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention before extraction with a chelating agent possess, in combination: a silica to alumina ratio of at least about 20; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 20 are useful, it is preferred to use catalysts having higher ratios of about 30, preferably 40.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 538° C. for a least 15 minutes. The catalyst is then flushed with helium and the temperature adjusted between 304° C. and 510° C. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

Constraint Index =
$$\frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12.

In the process according to this invention $C_2$ to $C_9$ olefinic hydrocarbons, such as propylene, are polymerized to produce an oligomerized liquid mixture from which is separated a fraction boiling above 343° C. which comprises a lubricating oil fraction with a high viscosity index. Typically, the polymerization is conducted between 179° C. to 343° C., but preferably at about 232° C. The polymerization pressure may range between 0.269 to 3.36 kPa, but preferably the polymerization is conducted at a pressure of about 1.10 kPa. Weight hourly space velocities for the polymerization can be between 0.1 to 10, but preferably 0.5, based on zeolite solids.

A key feature at the present invention is the use of a zeolite catalyst that has been extracted with a metal chelating agent in order to catalyze light olefin oligomerization to lubricant oil in high yield. Preferably, an extracted aluminosilicate, such as ZSM-5, is used. Any conventional method of extracting aluminum from large or small pore zeolites can be used to extract framework aluminum from the intermediate pore size zeolites of the present invention.

We prefer to extract aluminum using a chelating agent or other complexing agent or some combination of approaches.

The starting material is usually in the hydrogen form for best removal of aluminum from the zeolite framework. The hydrogen form may be generated in-situ, e.g., if an acid is used for the aluminum extraction, the H-form is made in-situ. Another way would be ion-exchange with $NH_4+$, calcination in the presence of water vapor or steam, causing removal of some Al from the framework, and finally ion-exchanging this, now cationic, Al with a salt, e.g., an $NH_4+$ salt. The latter ion-exchange can be facilitated by using a chelating agent, e.g., $(NH_4)_2 H_2 EDTA$, for the $NH_4+$ exchange. The EDTA removes the $Al^{3+}$ ions from the ion-exchange equilibrium by complexing. $(NH_4)_2 H_2 EDTA$ does not remove framework-Al, while $H_4 EDTA$ does.

When we talk about aluminum sites, we usually mean tetrahedral or framework sites. These sites are not associated with water of hydration. But when this Al is hydrolyzed out of the framework, then the small $Al^{3+}$ cations, of high charge density, are surrounded by water of hydration.

The preferred approach to aluminum removal is use of a chelating agent such as ethylenediaminetetraacetic acid, EDTA, nitrilo triacetic acid, NTA, ethylenediamine, glycine, 2, 4-pentanedione or other chelating agents. The chelating agent, e.g., EDTA, does not go into the zeolite pores. It only removes the $Al^{3+}$, migrating out of the pores, from the ion-exchange equilibrium by complexing. Thus, the chelating agent does not actually remove the Al from the framework. This latter reaction is caused by the reaction of the H+ *form with water (hydrolysis)*.

The minimum amount of chelating agent that must be added is that required by stoichiometry to remove the desired amount of aluminum from the zeolite framework. The upper limit on amount of chelating agent that is added is set more by economics than anything else. It is possible to operate with a tremendous excess of chelating agent and shorten the amount of time, or temperature, required for aluminum extraction.

The preferred chelating agent is EDTA. It is preferred to operate with 1 to 10 times the EDTA required by stoichiometry. The process can be conducted simply in a container with water, at temperatures of 50° to 250° C., with pressure sufficient to maintain a liquid phase.

At least some aluminum removal is necessary. Significant improvement in activity occurs in some zeolites with a constraint index of 1 to 12, and a silica alumina ratio greater than 20, when only 5% of the zeolite alumina is removed. Preferably 10 to 90% is removed. Most preferably, about 25% $Al_2O_3$ is removed.

Conventional catalyst finishing steps may be used with the catalyst of the instant invention. For instance, the catalyst may be steamed prior to use.

A surprisingly advantageous aspect of the present invention is the combined improvement of yield and viscosity index. The viscosity index of a hydrocarbon lubricant oil fraction is related to its molecular conformation. Extensive branching in a molecule usually results in a low viscosity index. It is believed that two modes of oligomerization/polymerization of olefins can take place over acidic zeolites such as HZSM-5. One reaction sequence takes place at Bronsted acid sites inside the channels or pores, producing essentially linear material. The other reaction sequence occurs on the outer surface, producing highly branched material. By decreasing the surface acid activity of such zeolites, fewer highly branched products with low viscosity index are obtained.

Several techniques may be used to increase the relative ratio of intracrystalline acid sites to surface active sites. This ratio increases with crystal size due to geometric relationships between volume and superficial surface area, deposition of carbonaceous materials by coke formation and by surface chemisorption of organic bases. Without wishing to be restricted by theoretical considerations, it is believed that extraction of $Al_2O_3$ from the zeolite type catalyst preferentially occurs on the catalyst surface as opposed to the catalyst pores. Accordingly, intracrystalline acid site olefin polymerization is enhanced in preference to surface active site polymerization leading to the formation of more linear lubricant range hydrocarbons with an attendant enhancement in viscosity index.

That this highly desirable improvement in molecular linearity is achieved with an accompanying substantial increase in yield of 343° C.+ lubricant fraction is an unexpected development distinguishing the invention.

The following examples serve to illustrate the practices and advantages of the present invention.

EXAMPLE 1

Pre-extraction HZSM-5 zeolite is prepared as follows:

A 250 g sample of small-size ZSM-5 ($SiO_2/Al_2O_3$ ~40) is sized to 8–10 mesh and calcined in a tube furnace in an ammonia stream to 600° C. and held at this temperature for one hour. The material is then cooled to room temperature in an ammonia stream. The product is exchanged three times with a solution being 0.1N in $NH_4Cl$ and 0.1 N in $NH_4OH$, using 50 cc/g, at room temperature with occasional stirring for two hours each. The material is then filtered, washed chloride-free and dried at ambient temperature. The product contains 4.5 wt. % $Al_2O_3$.

EXAMPLE 2

Propylene processing using unextracted ZSM-5.

The zeolite from example 1 (no binder) is sized to 14–25 mesh and calcined 3 hours at 538° C. 4.9 g (9.3 cc) is placed in a ⅜" I.D. stainless steel reactor and treated with flowing hydrogen at 482° C. and atmospheric pressure for 1 hour to ensure a standard dried condition before introduction of the olefin. Propylene is then processed over the catalyst at 1.01 kPa, 0.5 WHSV, ~204° C. for a total of five days with the following results:

| Days on stream | −1 | −2 | −3 | −4 | −5 |
| --- | --- | --- | --- | --- | --- |
| Avg. Cat. Temp., °C. | 205 | 205 | 205 | 204 | 204 |
| Mat. Bal. Time, Hours | 16.5 | 27 | 19 | 24 | 24 |

-continued

| Days on stream | −1 | −2 | −3 | −4 | −5 |
| --- | --- | --- | --- | --- | --- |
| Liquid Product, wt % | 96.7 | 99.0 | 97.1 | 97.5 | 97.7 |
| Yields, wt % | | | | | |
| $C_1 + C_2$ | <0.1 | <0.1 | <0.1 | <0.1 | <0.1 |
| $C_3$ | 2.0 | 0.3 | 1.6 | 1.7 | 1.7 |
| $C_4$ | 1.5 | 0.6 | 1.8 | 1.1 | 1.0 |
| $C_5$ | 1.4 | 1.3 | 1.7 | 1.3 | 1.1 |
| $C_6$–165° C. | 11.4 | 13.7 | 13.3 | 11.5 | 10.6 |
| 165–343° C. | 34.0 | 43.0 | 49.3 | 49.9 | 52.9 |
| 343° C.+ | 44.7 | 41.1 | 32.3 | 34.5 | 32.7 |

The liquid products are composited and distilled to give a 38 wt % yield of bottoms lubricant product having the following properties:

| Gravity, °API | 37.6 |
| --- | --- |
| Specific | 0.8368 |
| Pour Point, °C. | −54 |
| KV @ 40° C., cs | 22.86 |
| KV @ 100° C., cs | 4.23 |
| SUS @ 38° C. | 120 |
| Viscosity Index | 79.1 |

A portion of this material is topped to remove 15% overhead and give a more viscous lube, overall 32 wt % yield, having the following properties:

| Gravity, °API | 36.9 |
| --- | --- |
| Specific | 0.8403 |
| Pour Point, °C. | <−54 |
| KV @ 40° C., cs | 28.20 |
| KV @ 100° C., cs | 4.81 |
| SUS @ 38° C. | 146 |
| Viscosity Index | 85.1 |

EXAMPLE 3

Extraction of ZSM-5 with ethylenediaminetetraacetic acid (EDTA). The procedure of Example 1 is repeated, and the product treated with 2.5 g EDTA in 200 g of water for 24 hours at 100° C. The washed and dried product is found by analysis to contain 3.5 wt % $Al_2O_3$, compared to 4.5 wt % for the unextracted zeolite of Example 1.

EXAMPLE 4

Propylene processing over extracted catalyst of the instant invention.

The zeolite from Example 3 (no binder) is sized to 14–25 mesh and calcined 3 hours at 538° C. 4.9 g (10.0 cc) is placed in the reactor and treated with hydrogen as in Example 2. Propylene is then processed over the catalyst under the same conditions used in Example 2 for a period of four days with the following results:

| Days on stream | −1 | −2 | −3 | −4 |
| --- | --- | --- | --- | --- |
| Avg. Cat. Temp., °C. | 203 | 206 | 206 | 206 |
| Mat. Bal. Time, Hours | 18 | 24 | 24 | 27 |
| TOS, Days | 0.8 | 1.8 | 2.8 | 3.9 |
| Liquid Product, wt % | 93.3 | 95.1 | 98.0 | 98.3 |
| Yields, wt % | | | | |
| $C_1 + C_2$ | 0.1 | 0.1 | 0.1 | 0.1 |
| $C_3$ | 1.2 | 2.1 | 0.9 | 0.9 |
| $C_4$ | 2.8 | 1.9 | 1.1 | 1.1 |
| $C_5$ | 2.6 | 1.8 | 0.9 | 0.4 |
| $C_6$–165° C. | 14.0 | 12.2 | 12.6 | 11.7 |
| 165–343° C. | 37.4 | 40.5 | 41.8 | 43.9 |

-continued

| Days on stream | −1 | −2 | −3 | −4 |
|---|---|---|---|---|
| 343° C.+ | 42.0 | 41.5 | 42.7 | 42.0 |

The yield of 343° C.+ product is constant at about 42 wt % over the four day period, in contrast to the results of Example 2 with the untreated catalyst where the yield dropped from 45 to 32 wt % in three days.

The liquid products are composited, and distilled to give a 47 wt % yield of bottoms lubricant product having the following properties:

| Gravity, °API | 37.6 |
|---|---|
| Specific | 0.8368 |
| Pour Point, °C. | −54 |
| KV @ 40° C., cs | 22.70 |
| KV @ 100° C., cs | 4.23 |
| SUS @ 38° C. | 119 |
| Viscosity Index | 82.8 |

Comparison with the results of Example 2 using the untreated zeolite shows the same viscosity lubricant with a higher yield, 47 vs 38 wt %, and higher viscosity index, 82.8 vs 79.1.

When a portion of the material of Example 4 is topped to remove 13% overhead, an overall 41 wt % yield of lubricant with the following properties is recovered:

| Gravity, °API | 36.9 |
|---|---|
| Specific | 0.8403 |
| Pour Point, °C. | −54 |
| KV @ 40° C., cs | 27.88 |
| KV @ 100° C., cs | 4.79 |
| SUS @ 38° C. | 145 |
| Viscosity Index | 86.2 |

Viscosity is the same as that of the topped material of Example 2 and the yield is higher 41% vs 32%. The viscosity index is also higher, 86.2 vs 85.1.

The lubricant range products of the instant invention can be reacted further with hydrogen to saturate olefinic bonds in the product produced by oligomerization of olefins. Saturation of residual olefinic bonds results in a stabilized structure and is accomplished by known hydrogenation techniques. In particular, the product of the instant invention can be hydrogenated in the presence of hydrogen using catalyst, such as Pt, Pd, Co, Mo, combinations thereof and the like.

While the invention has been set forth herein by specific examples, there is no intent to limit the inventive concept as set forth in the following claims.

What is claimed is:

1. In the process of converting light olefins to lubricant range hydrocarbons comprising contacting such at high pressure and elevated temperature with a medium pore size shape selective metallosilicate zeolite catalyst having Bronsted acid activity, to produce a $C_{20}+$ hydrocarbon fraction comprising a major portion of 343° C.+ lubricant range hydrocarbons, the improvement comprising, contacting said light olefins with said metallosilicate zeolite catalyst, said catalyst having been extracted with a metal chelating agent, whereby 343+° C. lubricant range hydrocarbons are produced having a viscosity index of at least 80 with yields of at least 40%.

2. The process of claim 1 wherein said zeolite consists essentially of acidic aluminosilicate having a constrain index of about 1 to 12 and a silica to alumina mole ratio of about 20 to 100.

3. The process of claim 1 wherein said metallosilicate zeolite catalyst has a post-extraction $Al_2O_3$ content of about 3.5 wt. % based on a pre-extraction $Al_2O_3$ content of about 4.5 wt. %.

4. The process of claim 1 wherein said zeolite catalyst is extracted with an aluminum chelating agent taken from the group consisting essentially of ethylenediaminetetraacetic acid (EDTA), the dialkali salt of EDTA, ethylenediamine, glycine, 2,4-pentanedione, and nitriloacetic acid.

5. An improved process for the conversion of light olefins to $C_{20}+$ lubricant range hydrocarbons in high yield, comprising:
providing an acidic medium pore size, shape selective aluminosilicate zeolite type catalyst having the structure of ZSM-5, said catalyst having been extracted with an aluminum chelating agent;
contacting a light olefins feedstream with said catalyst in a fixed bed reactor under oligomerizing conditions to produce an effluent stream comprising a major portion of $C_{20}+$ hydrocarbons;
separating a 343° C+ fraction of said effluent stream to provide lubricant range hydrocarbons with viscosity index of at least 80 and yield of at least 40%.

6. The process of claim 5 further comprising the step of hydrogenating said lubricant range hydrocarbons to provide stabilized lubricant oil of high viscosity index.

7. The process of claim 5 wherein said oligomerizing conditions comprise pressure between 0.27 and 3.36 kPA, temperature between 177° C. and 343° C., and WHSV between 0.1 and 1.0.

8. The process of claim 5 wherein said oligomerizing conditions comprise pressure of about 1.0 kPA, temperature of about 200° C., and WHSV of about 0.5.

9. The process of claim 5 wherein said zeolite catalyst is extracted with an aluminum chelating agent taken from the group consisting essentially of ethylenediaminetetraacetic acid (EDTA), the dialkali salt of EDTA, ethylenediamine, glycine, 2,4-pentanedione and nitriloacetic acid.

10. The process of claim 5 wherein said zeolite type catalyst is extracted with EDTA.

11. The process of claim 5 wherein the light olefins feedstream comprises $C_3$ to $C_9$ olefins.

12. The process of claim 5 wherein the light olefins feedstream consists essentially of propylene and/or butene.

13. The process of claim 5 wherein said catalyst has a constrain index of about 1 to 12 and a silica to alumina mole ratio greater than about 20.

14. The process of claim 5 wherein the framework $Al_2O_3$ content of said extracted aluminosilicate zeolite catalyst is about 3.5 wt. % based on unextracted catalyst $Al_2O_3$ content of about 4.5 wt. %.

15. The process of claim 5 wherein said aluminosilicate catalyst is ZSM-5.

16. The process of claim 15 wherein said ZSM-5 catalyst has a crystallite size of 0.2 to 0.05 microns prior to extraction with said aluminum chelating agent.

* * * * *

UNITED STATES PATENT AND TRADEMARK OFFICE
CERTIFICATE OF CORRECTION

PATENT NO.   :   4,788,375
DATED        :   November 29, 1988
INVENTOR(S)  :   William E. Garwood, Guenter G. Kuehl and Rene B. LaPierre It is certified that error appears in the above-identified patent and that said Letters Patent is hereby corrected as shown below:

Column 1, line 50, "silia to aluminia" should be --silica to alumina--.

Column 2, line 17, insert --.-- between "$Al_2O_3$" and "Contacting".

Column 2, line 57, "elevaed" should be --elevated--.

Column 8, claim 2, line 4 "constrain" should be --constraint--.

Column 8, claim 4, line 15, remove "," preceding "and".

Column 8, claim 9, line 4, "witb" should be --with--.

Column 8, claim 13, line 55, "constrain" should be --constraint--.

Column 8, claim 16, line 64, "0.2" should be --0.02--.

Signed and Sealed this

Twenty-ninth Day of August, 1989

Attest:

DONALD J. QUIGG

Attesting Officer

Commissioner of Patents and Trademarks